United States Patent [19]

Ueda et al.

[11] Patent Number: 5,547,679
[45] Date of Patent: Aug. 20, 1996

[54] TAPE FOR HEAT VAPORIZATION OF ACTIVE AGENTS AND METHOD FOR VAPORIZING ACTIVE AGENTS BY HEATING

[75] Inventors: Minoru Ueda, Toyonaka; Ken-ya Okada, Takarazuka, both of Japan

[73] Assignee: Sumitomo Chemical Company, Limited, Osaka-fu, Japan

[21] Appl. No.: 272,739

[22] Filed: Jul. 11, 1994

[30] Foreign Application Priority Data

Jul. 29, 1993 [JP] Japan .................................. 5-187965
Mar. 31, 1994 [JP] Japan .................................. 6-063027

[51] Int. Cl.⁶ .................................................. A61L 9/03
[52] U.S. Cl. .............................................. 424/402; 424/404
[58] Field of Search ................................... 424/404, 402

[56] References Cited

FOREIGN PATENT DOCUMENTS

| 0239802 | 10/1987 | European Pat. Off. . |
| 1080242 | 3/1989 | Japan . |
| 2122903 | 1/1984 | United Kingdom . |
| 2166957 | 5/1986 | United Kingdom . |

Primary Examiner—Thurman K. Page
Assistant Examiner—Sharon Howard
Attorney, Agent, or Firm—Birch, Stewart, Kolasch & Birch, LLP

[57] ABSTRACT

There is disclosed a tape including a base layer containing substantially no active agent and a coating film layer containing a heat-vaporizable active agent and being formed on one side of the base layer by application of a coating containing the active agent. Also disclosed is a method of heat vaporizing an active agent which comprises moving the tape on a heater element while allowing the non-coated side of the base layer of the tape to come into contact with the heater element.

13 Claims, 2 Drawing Sheets

TAPE FOR HEAT VAPORIZATION OF ACTIVE AGENTS AND METHOD FOR VAPORIZING ACTIVE AGENTS BY HEATING

FIELD OF THE INVENTION

The present invention relates to a tape used for the heat vaporization of active agents such as insecticides, bactericides, fungicides and aromatizing agents. It also relates to a method for vaporizing these agents by heating the tape.

BACKGROUND OF THE INVENTION

The vaporization of insecticides has hitherto been effected by electrically heating the so-called mosquito-killing mat. In usual cases, the mat is effective only for about 8 hours, and it is, therefore, necessary to change the mat many times to maintain insecticidal effect for a long period of time.

There can be found several methods for the prolonged heat vaporization of an active agent by allowing a tape impregnated with the agent to pass through a heater element (see, e.g., JP-Y 51-51884/1976, JP-B 55-43727/1980, JP-A 57-155935/1982, JP-Y 4-4538/1992, JP-Y 4-4539/1992, JP-Y 4-4540/1992, JP-B 4-34362/1992).

However, these methods for the prolonged heat vaporization of an active agent have not yet been widely used up to the present.

SUMMARY OF THE INVENTION

Under these circumstances, the present inventors have intensively studied a method for the prolonged heat vaporization of an active agent. As the result, they have found the fact that relatively high temperatures are usually required to completely vaporize an active agent by heating a tape impregnated with the active agent, which may cause partial vaporization or decomposition of the active agent, resulting in a decreased efficiency for vaporization, and succeeded in developing an improved tape from which the active agent can be effectively and stably heat-vaporized for a long time, thereby completing the present invention.

Thus, the present invention provides a tape comprising a base layer containing substantially no active agent and a coating film layer containing a heat-vaporizable active agent and being formed on one side of the base layer by applying a coating containing the active agent onto the base layer.

It also provides a method for heat-vaporizing an active agent from the tape by moving the tape on a heater element while allowing the non-coated side of the base layer of the tape to come into contact with the heater element.

It further provides a method for pest control which comprises vaporizing a heat-vaporizable pest controlling agent by moving said tape having a coating film layer containing said active agent on a heater element.

The tape of the present invention shows high vaporization efficiency of the active agent from the tape at a suitable temperature. Further, the tape of the present invention can be produced easily and efficiently.

DETAILED DESCRIPTION OF THE INVENTION

Figure 1:
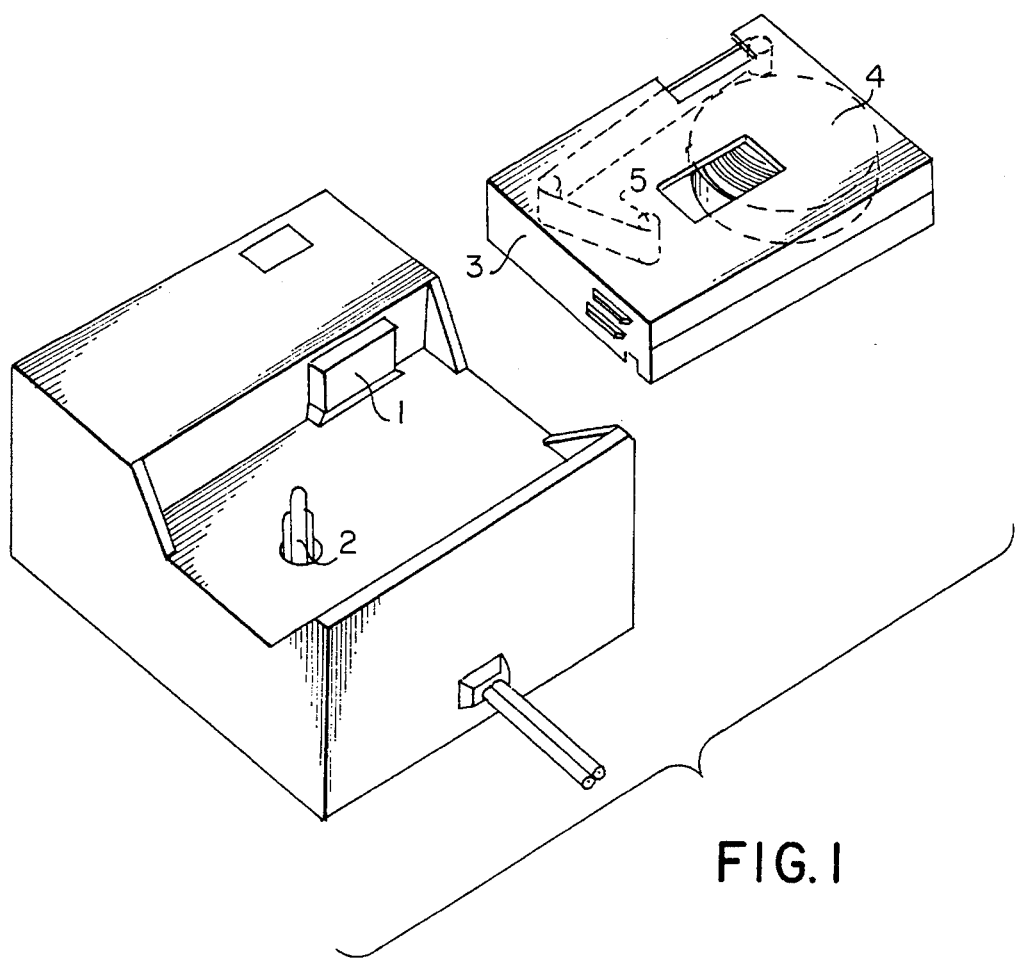
FIG. 1 is a perspective view showing a device used for the heat vaporization method of the present invention.

The tape of the present invention has a double-layer structure which is composed of a base layer containing substantially no active agent and a coating film layer containing an active agent and being formed on one side of the base layer by application of a coating containing the active agent.

The active agent to be used in the present invention is not particularly limited, so long as it can be vaporized by heating. However, the present invention is particularly effective for vaporization of insecticides, fungicides and aromatizing agents.

Examples of the insecticide are those used for controlling insanitary insects, including pyrethroid compounds such as allethrin, resmethrin, prallethrin, furamethrin, phenothrin, cyphenothrin, permethrin, cypermethrin, empenthrin and benfluthrin, including their effective isomers thereof; organic phosphorous compounds such as dimethyl dichlorovinyl phosphate (DDVP) and fenitrothion; carbamate compounds such as propoxur; and arylazole compounds such as fipronil.

In addition to these insecticides, agricultural and horticultural insecticides for use in greenhouses, including pyrethroids such as fenpropathrin and fluvalinate; organic phosphorous compounds such as chlorpyrifos, diazinon and chorobenzilate, may be used as the active agent of the present invention.

Examples of the fungicide used in the present invention are chlorothalonil, triadimefon, triflumizole, vinclozolin, anilazine and procymidone.

As the aromatizing agents, commercially available aromatizing agents may be used for the present invention.

These active agents may be used alone or in combination with various additives such as efficacy enhancing agents, stabilizers, pigments and fragrance.

The base layer is preferably made of a material which is resistant to heat and infiltration of the active agent and which does not easily transfer the active agent. Examples of the material for the base layer are synthetic resins such as polyethylene terephthalate (PET), polyfluoroethylene, polyimide and polyamide; reinforced materials of these resins with glass fibers; aluminum foil; and aluminum-laminated films.

The width, length and thickness of the base layer may be selected so as to attain the purpose of use, depending upon the kind of material therefor, agent to be used, kind and amount of coating to be applied, and conditions of use, such as time and place for use. However, the thickness of the base layer is, for example, in the range of about 10 to 100 μm, and the width thereof is, for example, in the range of about 6 to 100 mm.

Examples of the coating which can be used for the formation of a coating film layer are oil paints such as boiled oils, oil varnishes and spirit varnishes; fibrous coating such as cellulosic enamels, varnishes and cellulosic resins; synthetic resin enamels and varnishes such as phenolic resin enamels and varnishes, alkyd resin enamels and varnishes, vinyl resin enamels and varnishes, epoxy resin enamels and varnishes, acrylic resin enamels, unsaturated polyester resin enamels and varnishes, polyurethane resin enamels and varnishes, silicone resin enamels and varnishes; fluoropolymer resin enamels and varnishes. The coating may further contain various additives which are usually used in conventional coatings. The active agent is dissolved or dispersed in these coatings, if necessary, with addition of a solvent.

The tape of the present invention can be produced, for example, by applying the coating as prepared above to a base layer containing substantially no active agent, followed by drying, and then, if necessary, cutting it in appropriate widths and lengths.

The application may be carried out by any conventional method which is usually employed for paper and films. For example, the coating may be applied using a gravure printer.

The amount of coating to be used in the present invention as the weight of coating film-forming substances without any solvent is usually about 0.2 to 2 times the weight of the active agent used.

The amount of active agent-containing coating to be applied to the base layer may vary depending upon the purpose and use conditions of the tape, and it is preferably in the range of about 3 to 1000 g/m$^2$. The weight of coating film layer after drying is preferably in the range of about 1 to 300 g/m$^2$. The thickness of the coating film layer may vary depending upon the use conditions of the tape of the present invention, and it is preferably in the range of about 10 to 600 µm, more preferably about 10 to 100 µm.

Figure 2:
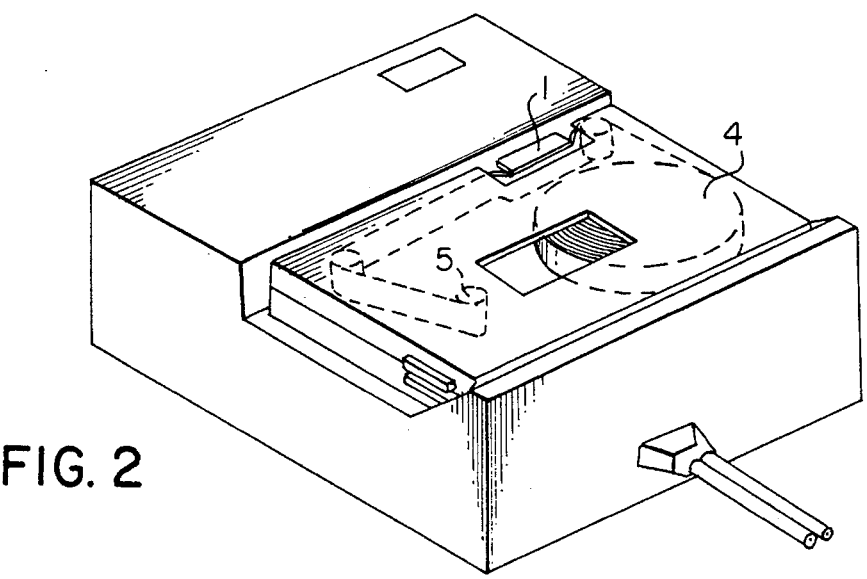
FIG. 2 is a perspective view showing the device of FIG. 1 as used.
Figure 3:
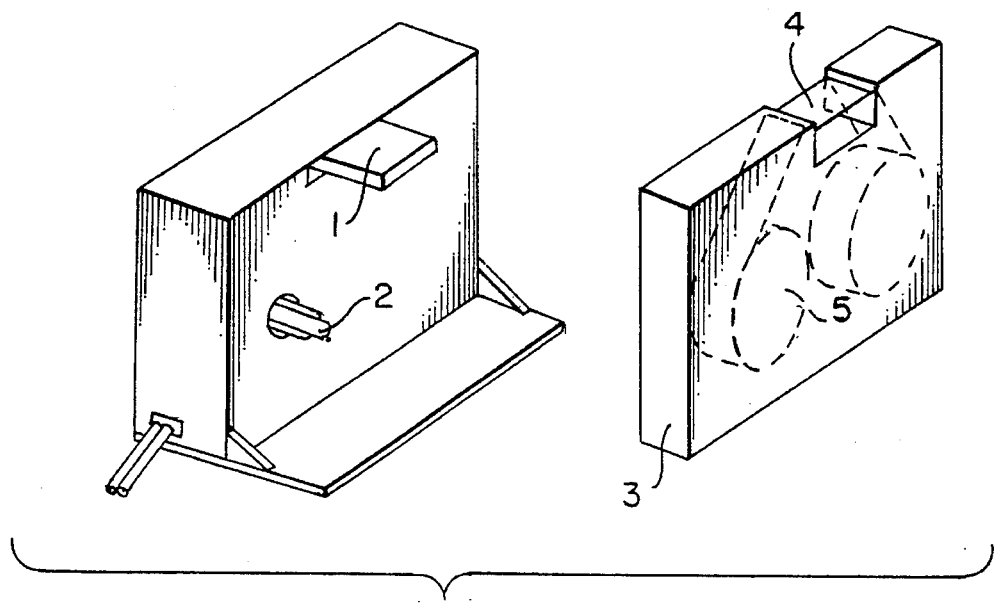
FIG. 3 is a perspective view showing another device used for the heat vaporization method of the present invention.
Figure 4:
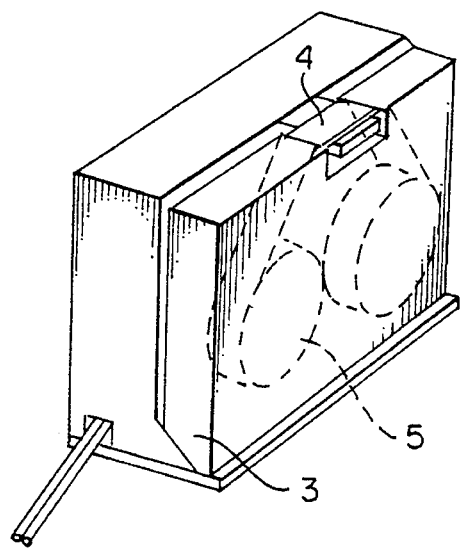
FIG. 4 is a perspective view showing the device of FIG. 3 as used.

FIG. 1 shows a device used for the heat vaporization of an active agent from the tape of the present invention. In this device, tape 4 is accommodated in cartridge 3 and provided in such a manner that it can be wound on to wind-up drum 5. FIG. 2 shows the device of FIG. 1 as used, in which case cartridge 3 is set on a heat vaporizing unit having a heater element 1 and wind-up shaft 2. FIG. 3 shows another device used for heat vaporization of an active agent from the tape of the present invention. FIG. 4 shows the device of FIG. 3 as used, in which case cartridge 3 is set on another heat vaporizing unit having a heater element 1 and wind-up shaft 2.

The surface temperature of the heater element may vary depending upon the kind of active agent to be used, and it is usually in the range of 40° to 300° C. In particular case where a pyrethroid compound is to be vaporized by heating, it is preferred that the heater element has a surface temperature of 80° to 300° C.

The running speed of the tape may vary depending upon various factors such as the size of the tape used and the amount of active agent contained in the coating film layer, and it is preferably in the range of 1 to 200 cm/hr.

The tape of the present invention can find various applications depending upon the properties of an active agent to be vaporized by heating. For example, in case where the active agent is an insecticide, bactericide or fungicide, the tape of the present invention can be used for pest control, for example, against insects such as mosquitoes, flies and cockroaches, fungi and other pests, by heat vaporization of the active agent therefrom.

EXAMPLES

The present invention will be further illustrated by the following examples, which are not to be construed to limit the scope of the present invention.

Example 1

To 3 parts by weight of a solution containing 24% by weight of a cellulosic resin in an organic solvent (a mixture of toluene, methyl ethyl ketone and ethyl acetate) was added 1 part by weight of an active agent (prallethrin), and the mixture was then applied to the surface of a PET film having a thickness of 25 µm as a base layer to form a coating film layer having a thickness of 15 µm. The amount of active agent contained in the coating film layer was 1 mg per 1.2 cm$^2$. The PET film having the coating film layer thereon was cut in the shape of a tape having a width of 1.2 cm, obtaining a tape for the heat vaporization of the active agent.

The tape thus obtained can be used for the vaporization of the active agent with high efficiency by allowing it to move on a heater element adjusted to about 160° C. in a device for heat vaporization as shown in FIG. 2 or 4.

Example 2

To 4 parts by weight of a solution containing 24% by weight of a cellulosic resin in an organic solvent (a mixture of toluene, methyl ethyl ketone and ethyl acetate) was added 1 part by weight of an active agent as shown in Table 1, and the mixture was then applied to the surface of a PET film having a thickness of 25 µm as a base layer to form a coating film layer. The PET film having the coating film layer thereon was cut in the shape of a tape having a width of 1.2 cm, obtaining a tape for the heat vaporization of the active agent.

The kind and application amount of active agent used, and the thickness of the coating film layer are also shown in Table 1.

TABLE 1

| Kind of active agent | Thickness of coating film layer (µm) | Amount of active agent (mg/cm$^2$) |
| --- | --- | --- |
| d-Allethrin | 15 | 0.97 |
| Bioaflethrin | 13 | 0.93 |
| Benfluthrin | 11 | 0.93 |
| d-Furamethrin | 17 | 1.1 |
| Prallethrin | 16 | 1.0 |

Example 3

To 2 parts by weight of a solution containing 20% by weight of a cellulosic resin in an organic solvent (a mixture of toluene, methyl ethyl ketone and ethyl acetate) was added 1 part by weight of an active agent (d-phenothrin), and the mixture was then applied to the surface of a polyimide film having a thickness of 40 µm as a base layer to form a coating film layer having a thickness of 40 µm. The amount of active agent contained in the coating film layer was 3 mg per 1.2 cm$^2$. The polyimide film having the coating film layer thereon was cut in the shape of a tape having a width of 5 cm, obtaining a tape for the heat vaporization of the active agent.

The tape thus obtained can be used for the vaporization of the active agent with high efficiency by allowing it to move on a heater element adjusted to about 230° C. at a rate of 1 cm/2 min.

Example 4

To 4 parts by weight of a solution containing 25% by weight of a polyurethane resin in an organic solvent (a mixture of toluene and isopropyl alcohol) was added 1 part by weight of an active agent as shown in Table 2, and the mixture was then applied to the surface of a polyimide film having a thickness of 40 µm as a base layer to form a coating film layer. The polyimide film having the coating film layer thereon was cut in the shape of a tape having a width of 1.2 cm, obtaining a tape for the heat vaporization of the active agent.

The kind and application amount of active agent used, and the thickness of the coating film layer are also shown in Table 2.

TABLE 2

| Kind of active agent | Thickness of coating film layer ($\mu$m) | Amount of active agent (mg/cm$^2$) |
|---|---|---|
| d-Allethrin | 12 | 0.74 |
| Bioallethrin | 17 | 0.82 |
| d-Furainethrin | 12 | 0.77 |
| Praflethrin | 14 | 0.82 |
| d-Phenothrin | 13 | 0.94 |
| Perinethrin | 12 | 0.82 |
| Cyphenothrin | 13 | 0.85 |

Example 5

The tape obtained in Example 1 was allowed to move on a heater element having a size of 2 cm×3 cm and adjusted to about 160° C., at a rate of 1 cm/hr, and the vapor was collected by absorption on a silica gel for 1 hour to determine the vaporization rate. It was found that the vaporization was carded out at a rate as high as 99%.

Example 6

The tape obtained in Example 1 was set on the device for heat vaporization of FIG. 3 in such a manner that it was able to move on a heating element adjusted to about 160° C. at a rate of 1 cm/hr, and the device was placed in a room having a size of 1.8 m×1.8 m×1.8 m for the knockdown test using 50 female adults of common mosquito (Culex pipiens pallens).

The $KT_{50}$ value (i.e., time to 50% knockdown of mosquitoes) was found to be 4.8 minutes.

Example 7

A tape for the heat vaporization of an active agent was obtained in the same manner as described in Example 2, except that RS-7836 (aromatizing agent made by Takasago International Corporation) was used as the active agent in place of the pyrethroid compounds as shown in Table 1.

Comparative Example 1

A piece of paper having a thickness of 0.1 mm was impregnated with prallethrin dissolved in acetone so as to absorb 1.1 mg of prallethrin per 1 cm$^2$ and dried. The paper obtained was cut in the shape of a tape having a width of 1.0 cm. The vaporization rate of the paper tape obtained was determined in the same manner as described in Example 5 and found to be 60%.

According to the heat vaporization method using a tape material of present invention, it is possible to vaporize a heat-vaporizable active agent with high efficiency, and it can, therefore, find various applications such as domestic use for the heat vaporization of insecticides or aromatizing agents and greenhouse use for the heat vaporization of insecticides, bactericides or fungicides.

What is claimed is:

1. A tape comprising a base layer containing substantially no active agent and a coating film layer containing a heat-vaporizable active agent and being formed on one side of the base layer by application of a coating containing the active agent, wherein the coating is a member selected from the group consisting of oil paint, fibrous coating, synthetic resin enamels and varnishes, and fluoropolymer resin enamels and varnishes; the heat-vaporizable active agent is a member selected from the group consisting of heat-vaporizable insecticides, bactericides, fungicides and aromatizing agents; and the base layer is made of synthetic resins or synthetic resins reinforced with glass fibers, aluminum foil or aluminum laminated films.

2. A tape according to claim 1, wherein the oil paint is a member selected from the group consisting of boiled oils, oil varnishes and spirit varnishes; the fibrous coating is a member selected from the group consisting of cellulosic enamels, varnishes and resins; the synthetic resin enamels and varnishes are a member selected from the group consisting of phenolic resin enamels and varnishes, alkyd resin enamels and varnishes, vinyl resin enamels and varnishes, epoxy resin enamels and varnishes, acrylic resin enamels and varnishes, unsaturated polyester resin enamels and varnishes, polyurethane resin enamels and varnishes, and silicone resin enamels and varnishes; and the synthetic resins used for making the base layer are selected from the group consisting of polyethylene terephthalate, polyfluoroethylene, polyimide and polyamide.

3. A tape according to claim 1, wherein the coating is member selected from the group consisting of cellulosic resin enamels and varnishes, and polyurethane resin enamels and varnishes.

4. A tape according to claim 1, wherein the active agent is insecticides or fungicides.

5. A tape according to claim 1, wherein the active agent is a pyrethroid compound, an organic phosphorus compound, a carbamate compound or an arylazole compound.

6. A tape according to claim 1, wherein the active agent is a pyrethroid compound.

7. A tape according to claim 1, wherein the active agent is allethrin.

8. A method for pest control which comprises vaporizing a heat-vaporizable insecticidal, bactericidal or fungicidal agent by moving a tape comprising a base layer containing substantially no active agent and a coating film layer containing the insecticidal, bactericidal or fungicidal agent and being formed on one side of the base layer by application of a coating containing the insecticidal, bactericidal or fungicidal agent on a heater element while allowing the non-coated side of the base layer of the tape to come into contact with the heater element, wherein the coating is a member selected from the group consisting of oil paint, fibrous coating, synthetic resin enamels and varnishes, and fluoropolymer resin enamels and varnishes; the heat-vaporizable active agent is a member selected from the group consisting of heat-vaporizable insecticides, bactericides, fungicides and aromatizing agents; and the base layer is made of unreinforced synthetic resins or synthetic resins reinforced with glass fibers, aluminum foil or aluminum laminated films.

9. A tape according to claim 1, wherein the active agent is prallethrin.

10. A tape according to claim 1, wherein the active agent is furamethrin.

11. A tape according to claim 1, wherein the active agent is permethrin.

12. A tape according to claim 1, wherein the active agent is benfluthrin.

13. A method of heat-vaporizing an active agent which comprises moving the tape set forth in claim 1 on a heater element while allowing the non-coated side of the base layer of the tape to come into contact with the heater element.

* * * * *